(12) United States Patent
Chacko et al.

(10) Patent No.: US 10,288,618 B2
(45) Date of Patent: May 14, 2019

(54) DIAGNOSIS OF CANCER BY DETECTING DIMERIC IL-18

(71) Applicant: Randox Laboratories Ltd., Northern Ireland (GB)

(72) Inventors: Alex Chacko, Northern Ireland (GB); Ivan McConnell, Northern Ireland (GB); Peter Fitzgerald, Northern Ireland (GB); John V. Lamont, Northern Ireland (GB)

(73) Assignee: RANDOX LABORATORIES LTD., Northern Ireland (GB)

( * ) Notice: Subject to any disclaimer, the term of this patent is extended or adjusted under 35 U.S.C. 154(b) by 0 days.

(21) Appl. No.: 15/302,849

(22) PCT Filed: Apr. 2, 2015

(86) PCT No.: PCT/GB2015/051052
§ 371 (c)(1),
(2) Date: Oct. 7, 2016

(87) PCT Pub. No.: WO2015/155513
PCT Pub. Date: Oct. 15, 2015

(65) Prior Publication Data
US 2017/0030917 A1    Feb. 2, 2017

(30) Foreign Application Priority Data

Apr. 9, 2014 (GB) .................................. 1406398.6
Jan. 28, 2015 (GB) .................................. 1501415.2

(51) Int. Cl.
| | | |
|---|---|---|
| G01N 33/53 | (2006.01) |
| G01N 33/574 | (2006.01) |
| A61P 35/00 | (2006.01) |
| A61P 35/04 | (2006.01) |
| G01N 33/68 | (2006.01) |
| C07K 14/54 | (2006.01) |

(52) U.S. Cl.
CPC ........ G01N 33/57484 (2013.01); A61P 35/00 (2018.01); A61P 35/04 (2018.01); G01N 33/53 (2013.01); G01N 33/57423 (2013.01); G01N 33/6869 (2013.01); C07K 14/54 (2013.01); G01N 2333/54 (2013.01); G01N 2800/52 (2013.01)

(58) Field of Classification Search
None
See application file for complete search history.

(56) References Cited

FOREIGN PATENT DOCUMENTS

GB    2324866 A  * 11/1998  ........... G01N 33/543

OTHER PUBLICATIONS

Dwivedi, Shailendra, et al., "Diagnostic and prognostic significance of prostate specific antigen and serum interleukin 18 and 10 in patients with locally advanced prostate cancer: a prospective study," Asian Pacific Journal of Cancer Prevention, J Cancer Prev, vol. 12, No. 7, Jan. 1, 2011, pp. 1843-1848.
Lunter, Pim, International Search Report and Written Opinion, International Application No. PCT/GB2015/051052, dated Jun. 15, 2015.
Okamoto, Masaki, et al., "Correlation of decreased survival and IL-18 in bone metastasis," Internal Medicine, May 15, 2009, pp. 763-773.
Shida, K, et al., "An alternative form of IL-18 in human blood plasma: complex formation with IgM defined monoclonal antibodies," the Journal of Immunology, vol. 166, No. 11, Jun. 1, 2001, pp. 6671-6679.
Carbone, Anna et al., "IL-18 Paradox in Pancreatic Carcinoma: Elevated Serum Levels of Free IL-18 are correlated with Poor Survival", J. Immunother., vol. 32, No. 9, Nov.-Dec. 2009.
Kikkawa Satomi et al., "A Comparative Analysis of the Antigenic, Structural, and Functional Properties of Three Different Preparations of Recombinant Human Interleukin-18", Journal of Interferon and Cytokine Research, 20:179-185 (2000).
Kikkawa Satomi et al., "Human Macrophages Produce Dimeric Forms of IL-18 which can be Detected with Monoclonal Antibodies Specific for Inactive IL-18", Biochemical and Biophysical Research Communications, 281, 161-467 (2001).
Seya, Tsukasa et al., "Protein polymorphism of human IL-18 identified by monoclonal antibodies", International Journal of Molecular Medicine, 8:585-590, 2001.
Seya, T. et al., "Novel Proforms of IL-18 are Produced in Human Langerhans Cells, Macrophages and Mature Dendritic Cells but not Monocytes", The Journal of Investigative Dermatology, 228 Abstracts.
Shida, Kyoko et al., "High serum levels of additional IL-189 forms may be reciprocally correlated with IgE levels in patients with atopic dermatits", Immunology Letters, 79 (2001), pp. 169-175.

* cited by examiner

Primary Examiner — Zachary C Howard
(74) Attorney, Agent, or Firm — Gavrilovich, Dodd & Lindsey LLP

(57) ABSTRACT

The present invention describes methods for screening for cancer in a subject, by measuring the level of dimeric IL-18 in a sample obtained from the subject, and comparing that level with the level in a normal control sample.
The present invention also describes an assay for screening for cancer in a subject, by measuring the level of dimeric IL-18 in a sample obtained from the subject, whereby an elevated level of dimeric IL-18 is indicative of cancer.

6 Claims, 17 Drawing Sheets

DIAGNOSIS OF CANCER BY DETECTING DIMERIC IL-18

CROSS REFERENCE TO RELATED APPLICATION

This application is a U.S. National Stage Application filed under 35 U.S.C. § 371 and claims priority to International Application No. PCT/GB2015/051052, filed Apr. 2, 2015, which application claims priority to Great Britain Application Nos. 1406398.6, filed Apr., 9, 2014 and 1501415.2 filed Jan. 28, 2016, the disclosures of which are incorporated herein by reference in their entireties.

FIELD OF THE INVENTION

This invention relates to the use of specific assays for diagnosing cancer. The invention is also directed to detection of metastases in subjects suffering from cancer.

BACKGROUND OF THE INVENTION

Neoplasms and cancer are abnormal growths of cells. Cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumours, are clusters of cells that are capable of growing and dividing uncontrollably. Tumours can be benign (noncancerous) or malignant (cancerous). Benign tumours tend to grow slowly and do not spread. Malignant tumours can grow rapidly, invade and destroy nearby normal tissues, and spread throughout the body. Malignant cancers can be both locally invasive and metastatic.

IL-18 (Interleukin-18) is a proinflammatory cytokine of the IL-1 superfamily. It was originally identified as being produced by macrophages in response to microbial lipopolysaccharide during infection. IL-18 binds to the IL-18 receptor (IL-18R), stimulating activation of other inflammatory cytokines such as IL-12, TNF-$\alpha$, and IFN-$\gamma$. The role of IL-18 has also been studied in relation to tumour biology, and increases in its expression have been shown to exert antitumour effects in mouse and cell line models (e.g. Lebel-Binay et al. (2003). Int J. Cancer 106, 827-835), possibly through induction of other proteins that induce tumour cell death, or through antiangiogenic properties.

Available immunoreagents specifically detect the monomeric form of IL-18, and they cannot be used to reliably diagnose cancer since the data they provide concerning monomeric IL-18 expression levels in cancer are inconsistent and often contradictory. In human tumours, some studies have suggested that monomeric IL-18 is moderately increased in non-small cell lung cancer, and that prostate tumours with a high proportion of cells staining positive for monomeric IL-18 had better prognosis. However, investigation of correlation between monomeric IL-18 levels and metastases has been less consistent. Okamoto and co-workers (Okamoto et al. (2009) Internal Medicine 48, 763-773) showed a modest but statistically significant increase in serum monomeric IL-18 from lung cancer patients with bone metastases, and Lissoni et al. (Lissoni et al. (2000). J Biol. Regul. Homeost. Agents, 14, 275-277) showed a similar result for lung cancer patients with stage IV (metastatic) disease. However, in colon cancer, reduced monomeric IL-18 levels correlated with distal metastases and poor prognosis (Pages et al. (1999) Int. J. Cancer 84, 326-330).

One important finding with implications for monitoring of IL-18 in disease is that alternative forms of IL-18 protein have been detected in human sera. These relate to homodimer (dimeric) and multimer (multimeric) complexes of IL-18 which form due to unusually strong disulphide bonds created between pairs of IL-18 molecules, and are readily detectable even in solutions of purified recombinant IL-18. It has been reported that the concentration of dimeric IL-18 in serum is up to 100-fold higher than the active, monomeric form (Seya et al. (2001) Int. J. Mol. Medicine 8, 585-590). Commercially available antibodies and immunoassays for detection of IL-18 only recognise the 18 kDa monomeric ligand or the 24 kDa pro-form monomer. They do not recognise dimeric IL-18 which appears to account for the majority of IL-18 in serum (Shida et al. (2001) J. Immunol. 166, 6671-6679).

Given the conflicting reports in the literature and the limitations of available reagents for detecting dimeric IL-18, current clinical data regarding the significance of IL-18 levels in various disease conditions, particularly serum IL-18, must be interpreted with caution.

There is a need for improved methods for the screening, diagnosis, prognostication and treatment of cancer, and a better understanding of the role of IL-18 as a biomarker of cancer and cancer metastasis.

SUMMARY OF THE INVENTION

The present invention is based on the finding that dimeric IL-18 is the predominant form of IL-18 seen circulating in the serum, and on the surprising finding that median levels of dimeric IL-18 measurable in samples from subjects suffering from cancer are sufficiently increased to allow reliable distinction between subjects suffering from cancer and healthy control subjects not suffering from cancer and between subjects suffering from cancer and other patients not suffering from cancer. The increase in median levels of dimeric IL-18 measurable in samples from subjects suffering from cancer is sufficiently large to allow for development of a sensitive assay to reliably identify subjects suffering from cancer. The present invention further provides an important improvement to the understanding of cytokine biology, and allows screening, diagnosis, prognosis and treatment of cancer to be made in a more focussed and effective way.

The understanding that dimeric IL-18 levels in serum are significantly higher than those of monomeric IL-18, and that levels of dimeric IL-18 are reliably correlated with the development of cancer, and further that the levels of dimeric IL-18 are correlated with tumour metastasis, allows cancers to be identified earlier and with less invasive methods while also permitting earlier and more effective therapeutic intervention by the clinician.

Thus, in a first aspect, the present invention is a method for screening for cancer in a subject, comprising measuring the amount of dimeric IL-18 in a sample obtained from the subject, and determining whether the amount of dimeric IL-18 is altered compared to a normal control.

In a second aspect, the present invention is a method for screening for metastases in a subject suffering from cancer, comprising measuring the amount of dimeric IL-18 in a sample obtained from the subject, and determining whether the amount of dimeric IL-18 is altered compared to a subject suffering from cancer and not having metastases.

In a third aspect, the present invention is a solid state device comprising a substrate comprising an antibody that binds to dimeric IL-18.

In a fourth aspect, the present invention is a method for determining the efficacy of a drug treatment for cancer, comprising measuring the amount of dimeric IL-18 in a sample obtained from the subject treated with the drug, comparing the measured amount of dimeric IL-18 to that of an untreated sample, and determining whether the drug has had the effect of altering the amount of dimeric IL-18.

In a fifth aspect, the present invention is a method for indicating the likelihood of successful response to a drug treatment for cancer, comprising stratifying subjects for treatment based upon the measured amount of dimeric IL-18 at or prior to the commencement of treatment.

DETAILED DESCRIPTION OF THE INVENTION

Figure 1:
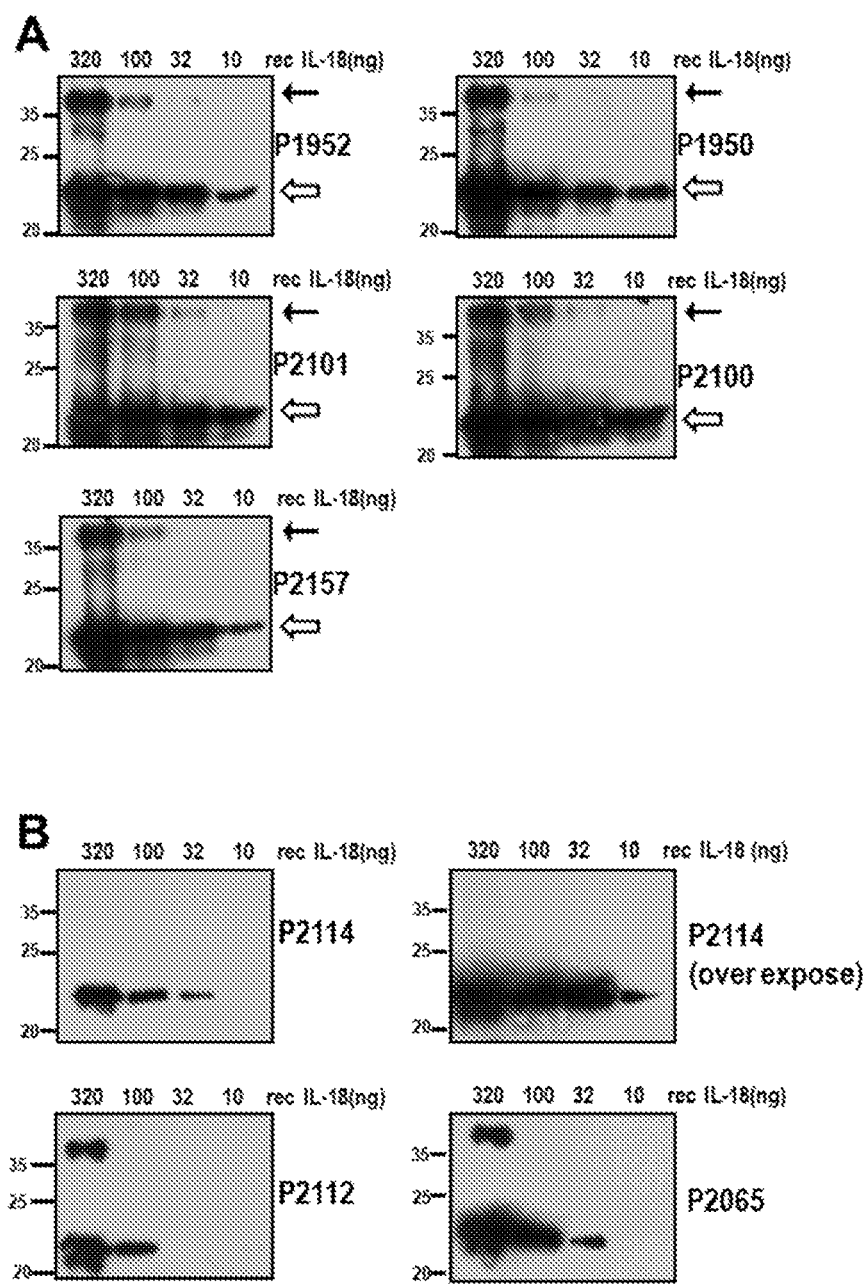
FIG. 1 shows recognition of monomeric recombinant IL-18 (open arrow) and dimeric recombinant IL-18 (closed arrow) by anti-IL-18 monoclonal antibodies. (A) Western blot analysis of recombinant IL-18 (320, 100, 32 or 10 ng/lane) using anti-IL-18 antibodies P1952, P1950, P2101, P2100 and P2157. (B) Western blot analysis of recombinant IL-18 (320, 100, 32 or 10 ng/lane) using anti-IL-18 antibodies P2114, P2112 and P2065. Anti-IL-18 antibody binding was visualised using a horseradish peroxidase conjugated secondary antibody.

The present invention is based on an appreciation of the dimeric nature of IL-18 present in serum and on effective measurement of dimeric IL-18 in samples from subjects suspected of or at risk of suffering cancer. The present inventors have identified the importance of measuring the levels of dimeric IL-18 for use as a marker for cancers in human subjects. This key feature of the present invention provides for accurate detection of cancer where levels of dimeric IL-18 are significantly increased compared to those of normal healthy subjects. This key feature of the present invention also provides for accurate detection of cancer where levels of dimeric IL-18 are significantly increased compared to those of patients suffering from other diseases. Additionally, and unexpectedly, the present invention discloses the use of increased dimeric IL-18 levels in subjects suffering from cancer to detect the presence of metastases. This is a significant breakthrough in cancer detection, prognostication and treatment as it allows patients at risk of suffering cancer and cancer patients with metastases to be identified at an early stage and therapies to be developed in a targeted way.

Notably, the inventors have demonstrated a large increase in levels of dimeric IL-18 measurable in samples from subjects suffering from cancer compared to samples from healthy subjects, and the inventors have demonstrated a large increase in levels of dimeric IL-18 measurable in samples from subjects suffering from cancer compared to samples from patients suffering from other diseases. These increases are observed consistently and are sufficiently large to permit reliable diagnosis of cancer in a subject—in direct contrast to any differences in measurable levels of monomeric IL-18 which are inconsistent and not of sufficient magnitude to permit reliable diagnosis of cancer in a subject.

The following definitions apply to terms used throughout this description and in relation to any of the aspects of the invention described herein.

The terms "patient" and "subject" are used interchangeably herein and refer to any animal (e.g. mammal), including, but not limited to, humans, non-human primates, canines, felines, rodents and the like, which is to be the recipient of the diagnosis. Preferably, the subject or patient is a human.

In the context of the present invention, a "control" or "control value" is understood to mean the level of a biomarker typically found in patients who do not have cancer or patients who do have cancer but do not have metastases. For the avoidance of doubt, a "control" or "control value" may be determined by measuring the level of a biomarker in a patient suffering from a disease that is not cancer, for example chronic obstructive pulmonary disease (COPD). The control level of a biomarker may be determined by analysis of a sample isolated from a person who does not have cancer or may be the level of the biomarker understood by the skilled person to be typical for such a person. The control value of a biomarker may be determined by methods known in the art and normal values for a biomarker may be referenced from the literature from the manufacturer of an assay used to determine the biomarker level.

The "level" of a biomarker refers to the amount, expression level or concentration of the biomarker within the sample. The level of a biomarker may also refer to the biomarker measurement expressed as a ratio or percentage of the level of one or more other analytes. The level of one or more such other analytes may remain consistent in the majority of samples or conditions. By way of example, the other analytes could be albumin, 62 -actin, total matrix protein, a matrix-soluble ion or monomeric IL-18 as measured with a standard IL-18 assay.

The level of a biomarker may also refer to the biomarker measurement expressed as a ratio or percentage of the level of one or more other analytes, where the level of the one or more other analytes is proposed to hold some biochemical significance to the clinical condition of interest.

As used herein, the term "screening" refers to the process of routinely testing an individual to detect the presence of a disease, in particular cancer. The subject is preferably an individual who has presented themselves for routine screening for cancer but who has not experienced or reported any symptoms of cancer nor been motivated to seek medical attention due to symptoms of cancer (i.e. the subject is asymptomatic for cancer). Alternatively or additionally, the individual may be at high risk of cancer, for example due to family history of cancer.

As used herein, references to "aiding diagnosis" may refer to aiding primary diagnosis, in the context of non-routine testing an individual to detect the presence of a disease, in particular cancer. In contrast to screening, in the context of diagnosis the patient is an individual who is presenting with symptoms of cancer or who has been motivated to seek medical attention due to symptoms of cancer. In certain embodiments, "aiding diagnosis" may also refer to stratification of a patient with a positive diagnosis of cancer, to further characterise the tumour.

As used herein, "symptoms of cancer" include, but are not limited to, appearance or increase in size of lumps, coughing, chest pain, breathlessness, unexplained bleeding, unexplained weight loss, loss of appetite, indigestion, nausea, excessive gas and a bloated feeling, unexplained weight gain or an increased waist size, swelling in the abdomen associated with shortness of breath, pain in the lower abdomen, changes in bowel or bladder habits, diarrhoea, constipation, or needing to pass urine more often and lower back pain.

As used herein, the term "a sample" includes biological samples obtained from a patient or subject, which may comprise blood, plasma, serum, urine, saliva or sputum.

The term "cancer" refers to or describes the physiological condition in mammals in which a population of cells are characterised by unregulated cell growth.

The terms "cancer cell" and "tumour cell" are grammatical equivalents referring to the total population of cells derived from a tumour or a pre-cancerous lesion. The terms "tumour" and "neoplasm" are used interchangeably herein and refer to any mass of tissue that results from excessive cell growth, proliferation and/or survival, either benign (noncancerous) or malignant (cancerous), including pre-cancerous lesions.

The methods of the invention described herein are carried out ex vivo. For the avoidance of doubt, the term "ex vivo" has its usual meaning in the art, referring to methods that are carried out in or on a sample obtained from a subject in an artificial environment outside the body of the subject from whom the sample has been obtained.

The term "metastasis" and related terms "metastases" and "metastatic" refers to a cancer or tumour that has spread from the original site in which it developed and has invaded and/or is growing in other tissues, forming new tumour growths and obstructions.

The terms "immunoassay", "immuno-detection" and immunological assay" are used interchangeably herein and refer to antibody-based techniques for identifying the presence of or levels of a protein in a sample. Examples of such assays and methods are well known to those of skill in the art.

The term "probe" refers to a molecule that is capable of specifically binding to a target molecule such that the target molecule can be detected as a consequence of said specific binding. Probes that can be used in the present invention include, for example, antibodies, aptamers and oligonucleotides.

The term "antibody" refers to an immunoglobulin which specifically recognises an epitope on a target as determined by the binding characteristics of the immunoglobulin variable domains of the heavy and light chains ($V_H$S and $V_L$S), more specifically the complementarity-determining regions (CDRs). Many potential antibody forms are known in the art, which may include, but are not limited to, a plurality of intact monoclonal antibodies or polyclonal mixtures comprising intact monoclonal antibodies, antibody fragments (for example $F_{ab}$, $F_{ab}$', and $F_v$ fragments, linear antibodies single chain antibodies and multi-specific antibodies comprising antibody fragments), single-chain variable fragments (sc$F_v$S), multi-specific antibodies, chimeric antibodies, humanised antibodies and fusion proteins comprising the domains necessary for the recognition of a given epitope on a target. Preferably, references to antibodies in the context of the present invention refer to monoclonal antibodies. Antibodies may also be conjugated to various detectable labels to enable detection, including but not limited to radionuclides, fluorophores, dyes or enzymes including, for example, horse-radish peroxidase and alkaline phosphatase.

The term "aptamer" refers to an oligonucleotide molecule or a polypeptide molecule that specifically binds to a target molecule. Oligonucleotide aptamers may be ribonucleotides (RNA) or deoxyribonucleotides (DNA) and typically consist of short strands of oligonucleotides. Polypeptide aptamers typically consist of short peptide domains that may be attached at one end or at both ends to a protein scaffold.

The term "epitope" refers to the portion of a target which is specifically recognised by a given antibody. In instances where the antigen is a protein, the epitope may be formed from either a contiguous or non-contiguous number of amino acids (linear' or 'conformation' epitopes respectively), whereby in the case of the latter, residues comprising the epitope are brought together in the three-dimensional fold of the polypeptide. An epitope typically comprises, but is not limited to, 3-10 amino acids in specific positions and orientations with respect to one another. Techniques known in the art for determining the epitope recognised by an antibody (specifically whether or not an epitope comprises a given residue) include but are not limited to, site-directed mutagenesis or the use of suitable homologous proteins to the target protein, in combination with techniques for determining specific recognition or lack thereof, as exemplified below. By way of example and not limitation, an epitope may be determined as comprising a given residue by comparative analysis with a control comprising specific recognition of the native (non-substituted) target protein by said antibody; wherein diminished binding and/or lack of specific recognition by said antibody when compared with said control identifies a given residue as forming part of an epitope. Furthermore, structural analyses of antibody-target protein complexes via x-ray crystallography and/or nuclear magnetic resonance (NMR) spectroscopy, or suitable derivatives thereof, may also be used to determine the residues which constitute an epitope.

The term "binds specifically", in the context of antibody-epitope interactions, refers to an interaction wherein the antibody and epitope associate more frequently or rapidly, or with greater duration or affinity, or with any combination of the above, than when either antibody or epitope is substituted for an alternative substance, for example an unrelated protein. Generally, but not necessarily, reference to binding means specific recognition. Furthermore, it is appreciated that an antibody may recognise more than one antigen specifically, for example, an antibody that specifically binds to dimeric IL-18 may also bind specifically to monomeric IL-18. Techniques known in the art for determining the specific binding of a target by a monoclonal antibody or lack thereof include but are not limited to, FACS analysis, immunocytochemical staining, immunohistochemistry, western blotting/dot blotting, ELISA, affinity chromatography. By way of example and not limitation, specific binding, or lack thereof, may be determined by comparative analysis with a control comprising the use of an antibody which is known in the art to specifically recognise said target and/or a control comprising the absence of, or minimal, specific recognition of said target (for example wherein the control comprises the use of a non-specific antibody). Said comparative analysis may be either qualitative or quantitative. It is understood, however, that an antibody or binding moiety which demonstrates exclusive specific recognition of a given target is said to have higher specificity for said target when compared with an antibody which, for example, specifically recognises both the target and a homologous protein.

Dimeric IL-18 levels were measured in samples obtained from healthy subjects and from subjects suffering from lung cancer (with and without bone or kidney metastases), prostate cancer and pancreatic cancer, using standard ELISA assay and a basic assay diluent (FIGS. 6-14). Standard ELISA assays are well-known and routine using commercially available formats and reagents (see e.g., "*Technical Guide for ELISA*" (2013) KPL Ltd. www.kpl.com).

ELISA assay methods can be refined by the inclusion of various diluent additives, which serve to neutralise interfering substances in the sample being tested (See e.g., Bjerner J, et al. (2002) *Clinical Chemistry* 48, 613-621). Such modifications may be desirable when, for example, samples isolated from patients may contain "heterophilic antibodies", and these can include so-called "human anti-mouse antibodies" or "human anti-sheep antibodies" (See e.g., "*Blockers and Diluents for Immunoassays*", Meridian Life Science Inc. http://meridianlifescience.com). This need often becomes apparent when an assay fails to display correct linearity on dilution of serum (a.k.a. parallelism. See, "*Interference Testing in Clinical Chemistry Approved Guideline*"—Second Edition. Vol. 27, no. 27. by Clinical and Laboratory Standards Institute).

These heterophilic antibodies in a sample can interfere with the assay by binding non-specifically to the capture or detector antibodies, or to both simultaneously. This can cause falsely elevated signals in healthy samples and/or falsely depressed signals in disease samples. This has the effect of reducing the clinical sensitivity and specificity of the assay as the respective clinical ranges of the disease and healthy sets overlap due to the false signals in certain samples.

Addition of anti-interference agents can reduce or remove these aberrant signals, allowing for enhanced clinical distinction between samples obtained from subjects suffering from disease and healthy subjects.

Figure 15:
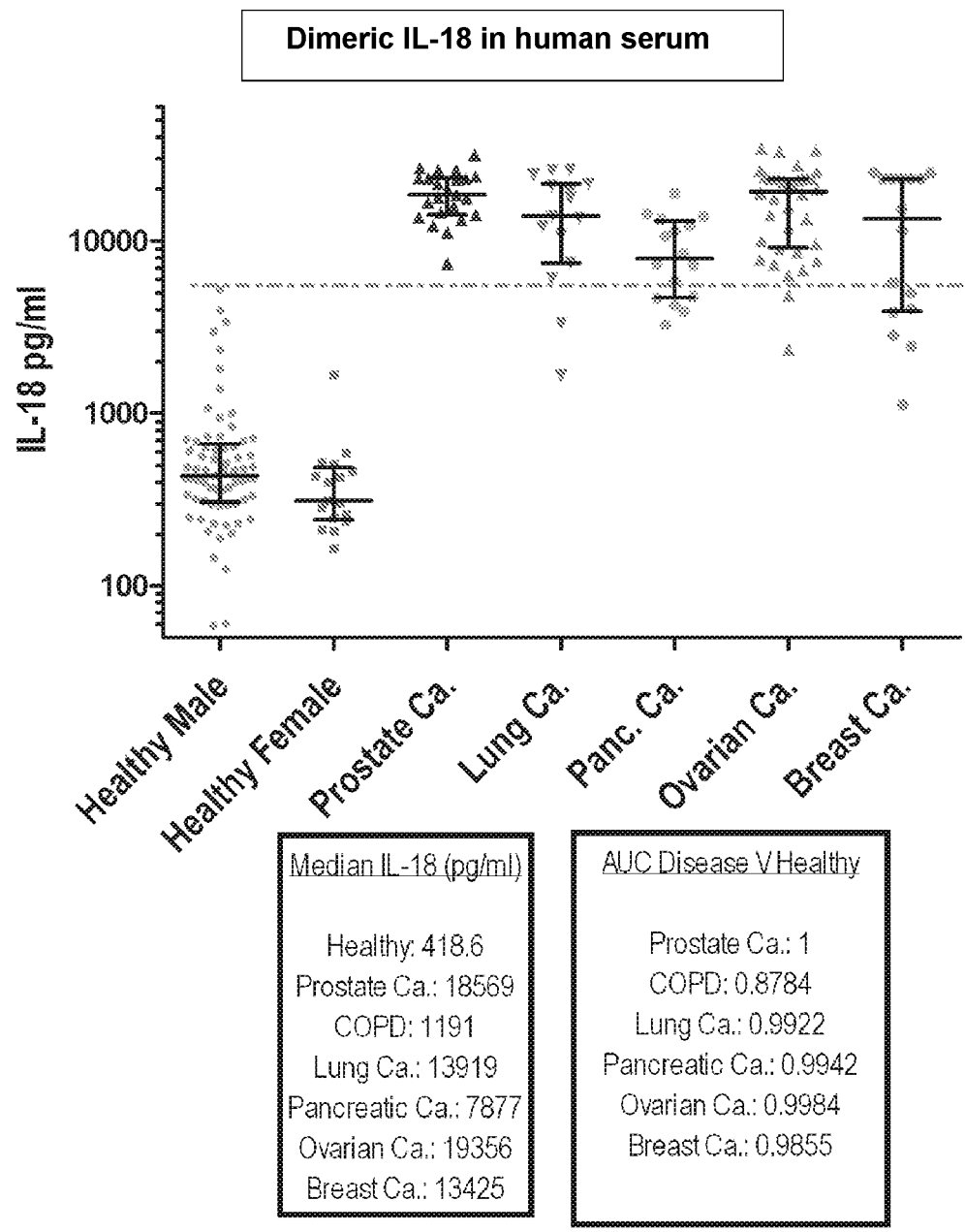
FIG. 15 shows that dimeric IL-18 levels are increased significantly in serum from patients suffering from prostate, lung, pancreatic, ovarian and breast cancers compared to serum from healthy subjects. In this study median levels of dimeric IL-18 were approximately forty fold higher in serum from prostate cancer patients compared to healthy controls (18569 pg/ml vs. 418.6 pg/ml), approximately thirty fold higher in serum from lung cancer patients compared to healthy controls (13919 pg/ml vs. 418.6 pg/ml), approximately twenty fold higher in serum from pancreatic cancer patients compared to healthy controls (7877 pg/ml vs. 418.6 pg/ml), approximately forty fold higher in serum from ovarian cancer patients compared to healthy controls (19356 pg/ml vs. 418.6 pg/ml), and approximately thirty fold higher in serum from breast cancer patients compared to healthy controls (13425 pg/ml vs. 418.6 pg/ml). The cut-off identified by a dashed line detects malignant disease with 100% specificity. Sensitivity at 100% specificity varies by disease as shown in Table 1.
Figure 16:
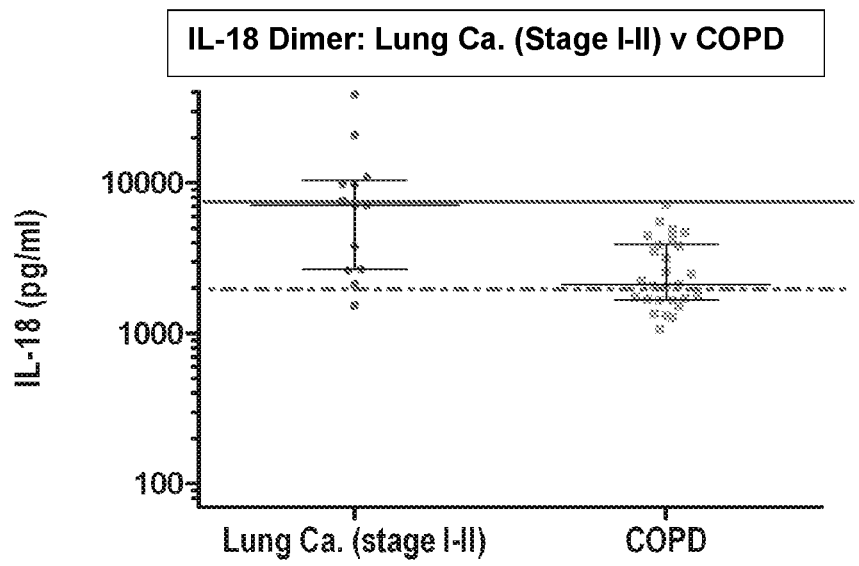
FIG. 16 shows that dimeric IL-18 levels are increased significantly in serum from patients suffering from stage I-II lung cancer compared to serum from patients suffering from chronic obstructive pulmonary disorder (COPD). Median levels of dimeric IL-18 were more than three-fold higher in serum from stage I-II lung cancer patients compared to serum from COPD patients (7088 pg/ml vs. 2109 pg/ml), while median levels of monomeric IL-18 were only marginally different between stage I-II lung cancer patients and COPD patients (357 pg/ml vs. 220 pg/ml). At cut-off of <2099 pg/ml dimeric IL-18, COPD will be indicated with 92.3% specificity and 48.2% sensitivity (dotted line). At cut-off of >7426 pg/ml, Lung cancer will be indicated with 100% specificity and 46.2% sensitivity (solid line).
Figure 16:
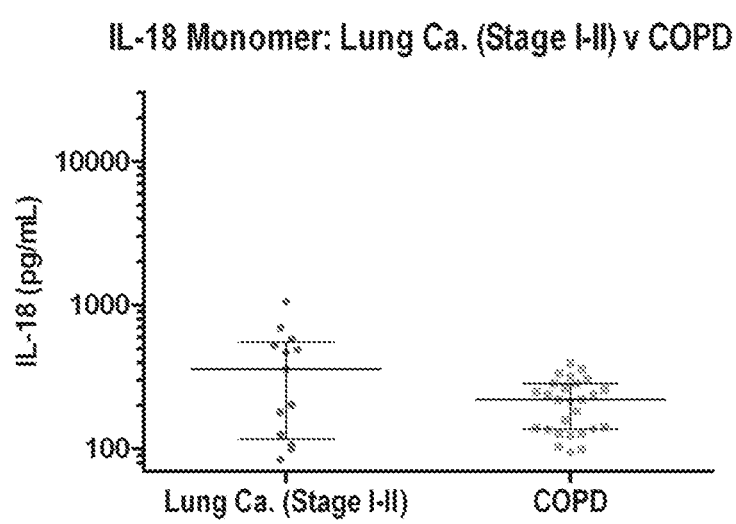

Such anti-interference agents include bovine gamma globulin (2 mg/ml), EDTA 0.025M, and sheep polyclonal IgG fraction (0.2 mg/ml) (FIGS. 15-17), as well as other non-specific immunoglobulin fractions.

A biomarker present in a sample isolated from a patient having cancer may have levels which are different to that of a control. However, the levels of some biomarkers that are different compared to a control may not show a strong enough correlation with cancer such that they may be used to diagnose cancer with an acceptable accuracy. Accuracy of a diagnostic method is often described by its receiver-operating characteristics (ROC) (Zweig, M. H., and Campbell, G., Clin. Chem. 39 (1993) 561-577). The ROC graph is a plot of all of the sensitivity/specificity pairs resulting from continuously varying the decision threshold over the entire range of data observed.

A ROC plot depicts the overlap between the two distributions by plotting the sensitivity versus 1—specificity for the complete range of decision thresholds. On the y-axis is sensitivity, or the true-positive fraction defined as [(number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always ≥0.5. Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0). In the context of the present invention, the two different conditions are whether a patient has or does not have cancer or alternatively whether a patient who has cancer has only a primary tumour or has metastatic disease. The ROC plot data and the clinical requirements of the test may be considered together when calculating a threshold or "cut-off" value to be used in future application of the diagnostic test. When the analyte value is measured above (or below) this cut-off value, the test is considered "positive" and further action may be taken appropriate to the clinical condition. An important feature in setting the cut-off value is the required specificity of the test (i.e. the true positive rate). By convention, the required specificity for many diagnostic tests is stated in advance to be 90%, 95%, or as close to 100% as practical. For cancer biomarker tests, it is likely that an effective test will need to approach 100% due to the relatively low prevalence of cancer in the general population (or even targeted populations) compared to those with inflammatory diseases and also on account of the severe consequences of false negative results for patients. The analyte cut-off value required to achieve these specificities may then be read from the ROC plot. This point on the plot will also denote a value for test sensitivity (true negative rate). Alternatively, the optimum cut-off value may be obtained by selecting the point on the ROC curve closest to the top-left corner of the graph.

Figure 7:
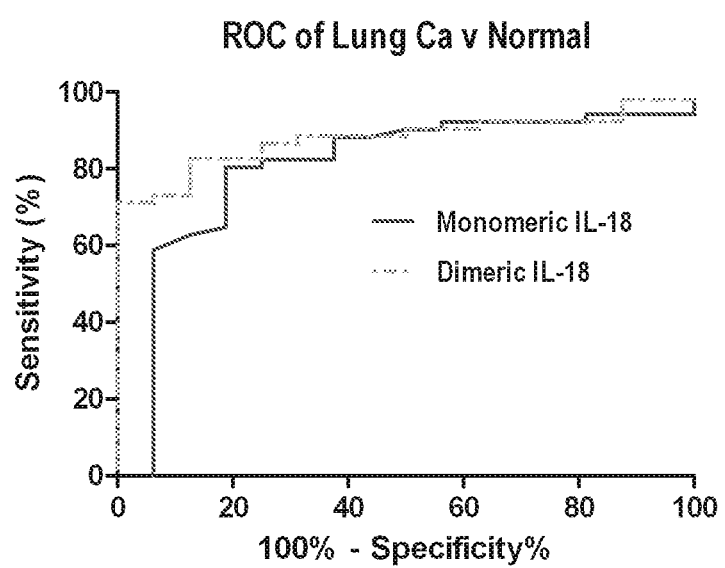
FIG. 7 shows overlaid Receiver Operator Curves for dimeric IL-18 levels and monomeric IL-18 levels in serum from a population of patients suffering from lung cancer compared to serum from a population of healthy subjects, which following binary logistic regression had AUC values of 0.880 (dimeric IL-18) and 0.800 (monomeric IL-18).
Figure 9:
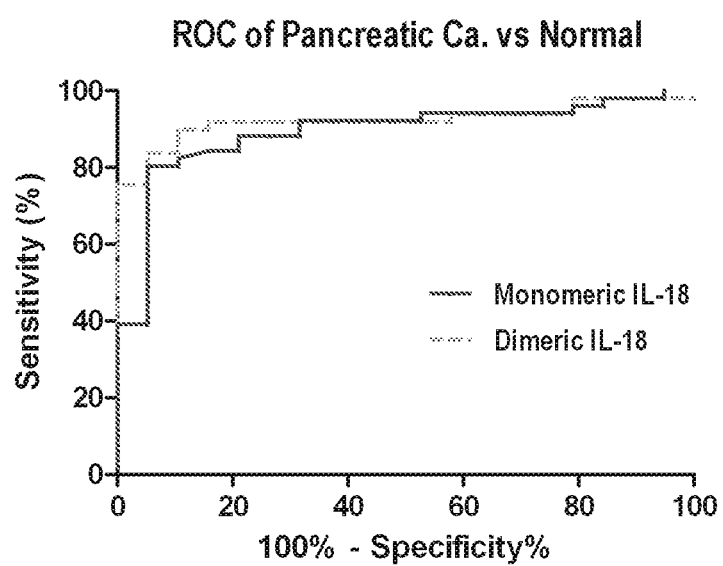
FIG. 9 shows overlaid Receiver Operator Curves for dimeric IL-18 levels and monomeric IL-18 levels in serum from a population of patients suffering from pancreatic cancer compared to serum from a population of healthy subjects, which following binary logistic regression had AUC values of 0.922 (dimeric IL-18) and 0.890 (monomeric IL-18).
Figure 11:
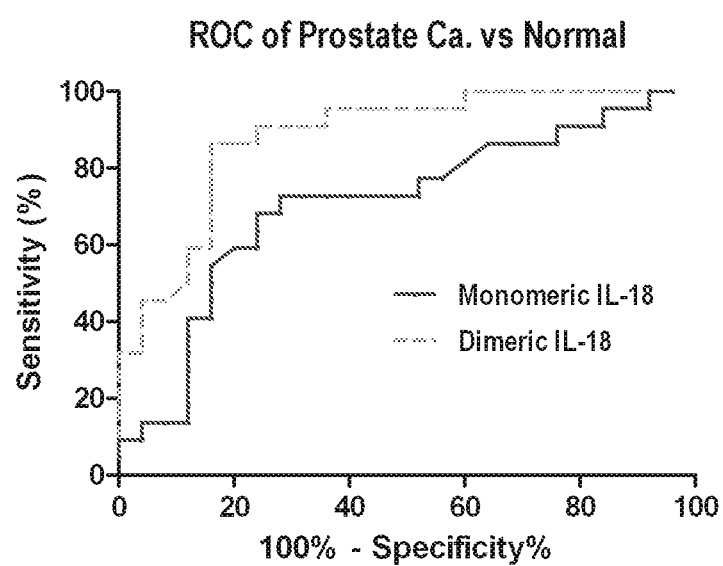
FIG. 11 shows overlaid Receiver Operator Curves for dimeric IL-18 levels and monomeric IL-18 levels in serum from a population of patients suffering from prostate cancer compared to serum from a population of healthy subjects, which following binary logistic regression had AUC values of 0.881 (dimeric IL-18) and 0.708 (monomeric IL-18).
Figure 17:
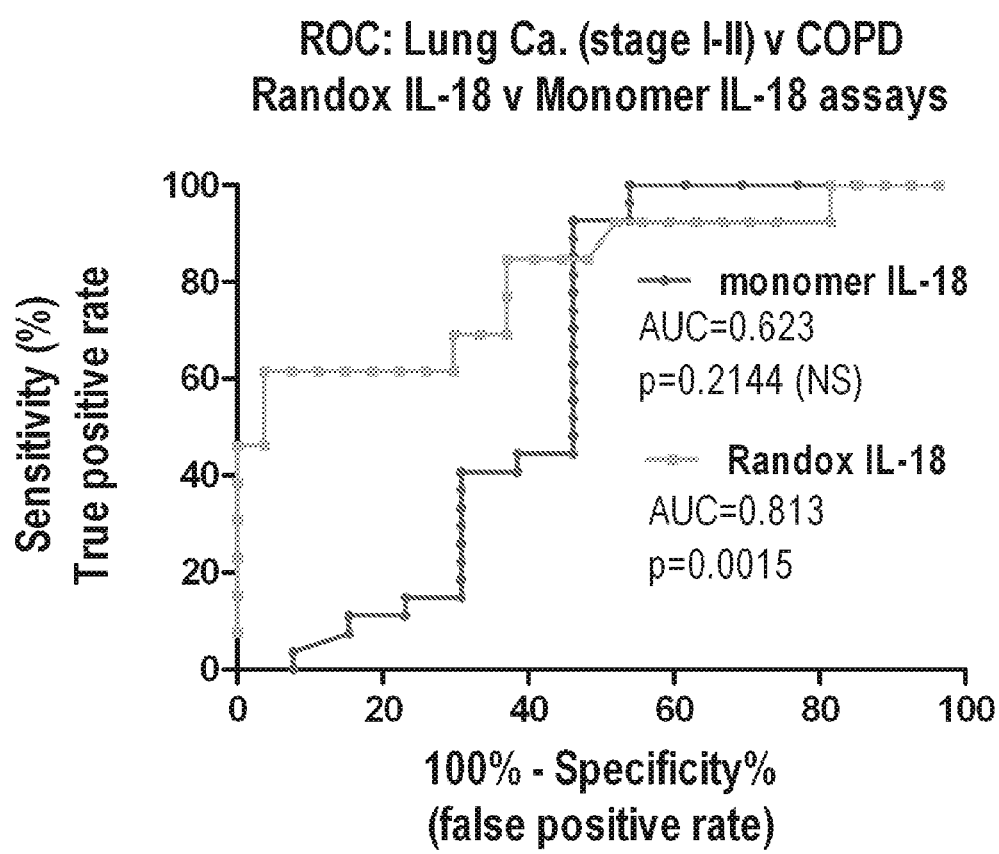
FIG. 17 shows overlaid Receiver Operator Curves for dimeric IL-18 levels and monomeric IL-18 levels in serum from a population of patients suffering from stage I-II lung cancer compared to serum from a population of COPD patients, which following binary logistic regression had AUC values of 0.813 (dimeric IL-18) and 0.623 (monomeric IL-18).

An effective diagnostic biomarker test will need to approach 100% specificity. Diagnostic tests that are 100% specific, i.e., that produce no false positive or false negative results, are considered ideal. However, a low level of false results can be acceptable, and so biomarkers demonstrating specificity close to 95% or above are often acceptable. As shown in FIGS. 7, 9 and 11 the points closest to the top-left of the ROC curves for dimeric IL-18 all fall close to or above 95% specificity. As shown in FIG. 17 the point closest to the top-left of the ROC curves for dimeric IL-18 falls close to or above 90% specificity. This feature allows the invention to work effectively in the clinic where a low level of false positives and false negatives is essential to permit effective diagnosis and treatment of patients.

In looking for specificity approaching 100% in distinguishing lung cancer patients from healthy subjects, the dimeric IL-18 assay gives 71.15% sensitivity at 100% specificity while the monomeric IL-18 assay only achieves a maximum of 93.75% specificity, which gives 58.82% sensitivity (FIG. 7). Taking the cut-off value as being the point closest to the top-left of the ROC curve, the lung cancer set tested for dimeric IL-18 gives 73.08% sensitivity at 93.75% specificity, while the monomeric IL-18 assay gives only 58.82% sensitivity at 93.75% specificity (see FIG. 7).

In looking for specificity approaching 100% in distinguishing stage I-II lung cancer patients from COPD patients, the dimeric IL-18 assay gives 46.2% sensitivity at 100% specificity while the monomeric IL-18 assay only achieves a maximum of 92.3% specificity, which gives 3.7% sensitivity (FIG. 17). Taking the cut-off value as being the point closest to the top-left of the ROC curve, the lung cancer set tested for dimeric IL-18 gives 61.5% sensitivity at 96.3% specificity, while the monomeric IL-18 assay gives only 53.9% sensitivity at 92.3% specificity (see FIG. 17).

In looking for specificity approaching 100% in distinguishing pancreatic cancer patients from healthy subjects and patients suffering from other diseases, the dimeric IL-18 assay gives 75.51% sensitivity at 100% specificity, while the monomeric IL-18 assay gives only 39.22% sensitivity at 100% specificity (FIG. 9).

In looking for specificity approaching 100% in distinguishing prostate cancer patients from healthy subjects and patients suffering from other diseases, the dimeric IL-18 assay gives 31.82% sensitivity at 100% specificity, while the monomeric IL-18 assay gives only 9.09% sensitivity at 100% specificity (FIG. 11). Applying a less stringent threshold and taking the cut-off value as being the point closest to the top-left of the ROC curve, the prostate cancer set tested for dimeric IL-18 gives 45.45% sensitivity at 96.00% specificity, while the monomeric IL-18 assay gives only 13.64% sensitivity at 96.00% specificity (see FIG. 11).

In the present invention optimal threshold values for diagnosis of cancer are chosen by selecting the point on the ROC curve closest to the top-left corner of the graph. Accordingly, in a method of the invention a level of dimeric IL-18 above a threshold value of 715 pg/ml in a sample obtained from a subject suspected of having prostate cancer is indicative of prostate cancer in the subject. Similarly, in a further method of the invention a level of dimeric IL-18 above a threshold value of 1025 pg/ml in a sample obtained from a subject suspected of having pancreatic cancer is indicative of pancreatic cancer in the subject. Additionally, in a method of the invention a level of dimeric IL-18 above a threshold value of 1575 pg/ml in a sample obtained from a subject suspected of having lung cancer is indicative of lung cancer in the subject.

In the present invention optimal threshold values for diagnosis of stage I-II lung cancer and for distinguishing between stage I-II lung cancer and COPD are chosen by selecting the point on the ROC curves closest to the top-left corner of the graph. Accordingly, in a method of the invention a level of dimeric IL-18 above a threshold value of 6307 pg/ml in a sample obtained from a subject suspected of having stage I-II lung cancer is indicative of lung cancer in the subject while a level of dimeric IL-18 below a cutoff value of 2099 pg/ml is indicative of COPD.

In the present invention there are optimal threshold values for identification of a risk of having cancer, such optimal threshold values being chosen by selecting the point on the ROC curve closest to the top-left corner of the graph. Accordingly, in a method of the invention a level of dimeric IL-18 above a threshold value of 715 pg/ml but below 1025 pg/ml in a sample is indicative of a risk of prostate cancer in the subject. Similarly, in a further method of the invention a level of dimeric IL-18 above a threshold value of 1025 pg/ml but below 1575 pg/ml in a sample obtained from a subject is indicative of a risk of prostate cancer or pancreatic cancer or both prostate and pancreatic cancer in the subject. Additionally, in a method of the invention a level of dimeric IL-18 above a threshold value of 1575 pg/ml in a sample obtained from a subject is indicative of a risk of prostate cancer or pancreatic cancer or lung cancer or any combination of two or more of lung, prostate and pancreatic cancer in the subject. Where a level of dimeric IL-18 above an optimal threshold as described above is measured in a sample from a subject, that subject should undergo further testing to confirm or to rule out the presence of cancer.

In the present invention there are optimal threshold values for identification of a risk of having stage I-II lung cancer and not COPD, such optimal threshold values are chosen by selecting the point on the ROC curves closest to the top-left corner of the graph. Accordingly, in a method of the invention a level of dimeric IL-18 above a threshold value of 6307 pg/ml in a sample obtained from a subject suspected of having stage I-II lung cancer is indicative of a risk of lung cancer in the subject while a level of dimeric IL-18 below a cutoff value of 2099 pg/ml is indicative of a low risk of malignancy.

Additionally, a level of dimeric IL-18 in a sample obtained from a subject suspected of having COPD or lung cancer below a cutoff value of 498 pg/ml is indicative that lung disease is unlikely to be present.

The present invention has identified that increased levels of dimeric IL-18 are measurable in samples obtained from subjects suffering from cancer. In particular, increased levels of dimeric IL-18 are measurable in samples obtained from subjects suffering from lung cancer, subjects suffering from prostate cancer and subjects suffering from pancreatic cancer. Additionally, increased levels of dimeric IL-18 are measurable in samples obtained from subjects suffering from ovarian cancer and subjects suffering from breast cancer. Furthermore, median levels of dimeric IL-18 measurable in samples from subjects suffering from cancer are sufficiently increased to allow reliable distinction between subjects suffering from cancer and healthy control subjects not suffering from cancer, and median levels of dimeric IL-18 measurable in samples from subjects suffering from cancer are sufficiently increased to allow reliable distinction between subjects suffering from cancer and patients suffering from other diseases but not suffering from cancer.

Additionally, the present invention has identified that dimeric IL-18 levels are increased in patients with advanced or metastatic disease compared with those suffering from early stage cancer or healthy patients and patients suffering from other diseases. This is a significant breakthrough in cancer detection and will provide for improved treatment as it allows patients at risk of suffering cancer to be identified and therapies to be developed in a targeted way.

A first aspect of the present invention provides a method for screening for cancer in a subject, comprising measuring the amount of dimeric IL-18 in a sample obtained from the subject, and determining whether the amount of dimeric IL-18 is altered compared to a normal control.

A second aspect of the present invention provides a method for screening for metastases in a subject suffering from cancer, comprising measuring the amount of dimeric IL-18 in a sample obtained from the subject, and determining whether the amount of dimeric IL-18 is altered compared to a subject suffering from cancer and not having metastases.

The sample may be a urine sample, blood sample, serum sample, plasma sample, saliva sample or sputum sample.

The determination of the level of dimeric IL-18 in the sample may be determined by immunological methods such as an ELISA-based assay. Preferably, the methods of the present invention use a solid-state device for determining the level of dimeric IL-18 in the sample isolated from the patient. The solid-state device comprises a substrate on which is immobilised an antibody that binds specifically to dimeric IL-18. Such antibodies may be immobilised at discrete areas of an activated surface of the substrate. The solid-state device may perform multi-analyte assays such that the level of dimeric IL-18 in a sample isolated from the patient may be determined simultaneously with the level of a further biomarker of interest in the sample. In this embodiment, the solid-state device has a multiplicity of discrete reaction sites each bearing a desired antibody covalently bound to the substrate, and in which the surface of the substrate between the reaction sites is inert with respect to the target biomarker. The solid-state, multi-analyte device may therefore exhibit little or no non-specific binding.

A third aspect of the present invention provides a solid-state device comprising a substrate comprising an antibody that binds specifically to dimeric IL-18.

A device that may be used in the invention may be prepared by activating the surface of a suitable substrate, and applying an array of antibodies on to discrete sites on the surface. If desired, the other active areas may be blocked. The ligands may be bound to the substrate via a linker. In particular, it is preferred that the activated surface is reacted successively with an organosilane, a bifunctional linker and the antibody. The solid-state device used in the methods of the present invention may be manufactured according to the method disclosed in, for example, GB-A-2324866 the contents of which is incorporated herein in its entirety. Preferably, the solid-state device used in the methods of the present invention is the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

A fourth aspect, the present invention is a method for determining the efficacy of a drug treatment for cancer, comprising measuring the amount of dimeric IL-18 in a sample obtained from the subject treated with the drug, comparing the measured amount of dimeric IL-18 to that of an untreated sample, and determining whether the drug has had the effect of altering the amount of dimeric IL-18.

In a fifth aspect, the present invention is a method for indicating the likelihood of successful response to a drug treatment for cancer, comprising stratifying subjects for treatment based upon the measured amount of dimeric IL-18 at or prior to the commencement of treatment.

TABLE 1

| Disease | Cut-off (pg/ml) | Sensitivity | Specificity |
|---|---|---|---|
| Prostate cancer | 6326 | 100% | 100% |
| Lung cancer | 5624 | 86.7% | 100% |
| Pancreatic cancer | 5564 | 68.8% | 100% |
| Pancreatic cancer | 4102* | 87.5% | 98.8% |
| Ovarian cancer | 5773 | 94.4% | 100% |
| Breast cancer | 5564 | 62.5% | 100% |
| Breast cancer | 3979* | 75.0% | 98.8% |

*Closest point to top left of ROC

The above values were calculated by GraphPad Prism software and are based on the value of the disease sample at the specificity given.

The invention is further described with reference to the following non-limiting example:

EXAMPLES

Antibody Detection of Dimeric IL-18

Monoclonal antibodies were raised against recombinant IL-18 using standard techniques. Affinity purified anti-IL-18 antibodies from individual hybridomas were tested by Western blot against recombinant IL-18 protein. Purified antibodies from 10 of 11 hybridomas tested showed strong detection of IL-18 at the expected size of about 22 kDa, and also showed reactivity to a heavier band at approximately 44 kDa (e.g., antibodies 1950, 1952, 2100, 2101 and 2157 shown in FIG. 1A). Antibodies P2100 and P2101 appeared to give the strongest signal for this 44 kDa protein relative to the monomeric IL-18 band, while P1950, P1952 and P2157 also detected the 44 kDa band, but at a relatively lower level. Purified antibodies P2112 and P2065 showed moderate detection of monomeric IL-18 and of the 44 kDa band, while purified antibody P2114 detected the monomeric IL-18 but was unable to detect the 44 kDa band (FIG. 1B).

Identification of 44 kDa IL-18 Homodimer

Figure 2:
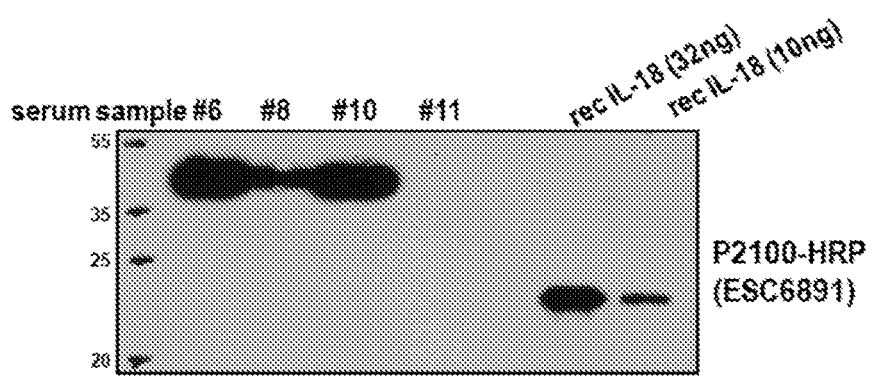
FIG. 2 shows predominance of dimeric IL-18 in serum and confirms IL-18 specificity of antibodies used in these studies. Western blot analysis of protein from serum samples #6, #8, #10 and #11 (25 µg/lane), and recombinant IL-18 using HRP-tagged anti-IL-18 antibody ESC6891. Antibody binding was visualised without using secondary antibodies.

Antibodies with reactivity against the ~44 kDa protein band detected this heavier protein band in three out of four human serum samples tested (FIG. 2). Interestingly, no monomeric IL-18 was detectable in the serum samples tested despite the antibodies being able to detect monomeric recombinant IL-18 on the same blot (FIG. 2). From this it is concluded that dimeric IL-18 is readily detectable in sera, and that detection of monomeric IL-18 protein in serum is minimal even on a reducing western blot.

Possible detection of contaminating protein by the secondary antibody used in Western blotting protocols was ruled out by detection of recombinant IL-18 under reducing and non-reducing conditions using anti-IL-18 antibodies conjugated directly to the horseradish peroxidase reporter (HRP) enzyme. Antibodies ESC6886, ESC6873 and ESC6891 that are HRP-conjugated forms of antibodies P2112, P1950 and P2100 respectively gave similar results. The HRP conjugated antibodies all reacted strongly with dimeric IL-18 in non-reducing conditions, and could even detect an apparent tetrameric form. Reduction by incubation at 100° C. in the presence of DTT abolished the tetrameric form but not the dimeric form (FIG. 3).

Detection of IL-18 Using Commercially Available Reagents

Figure 3:
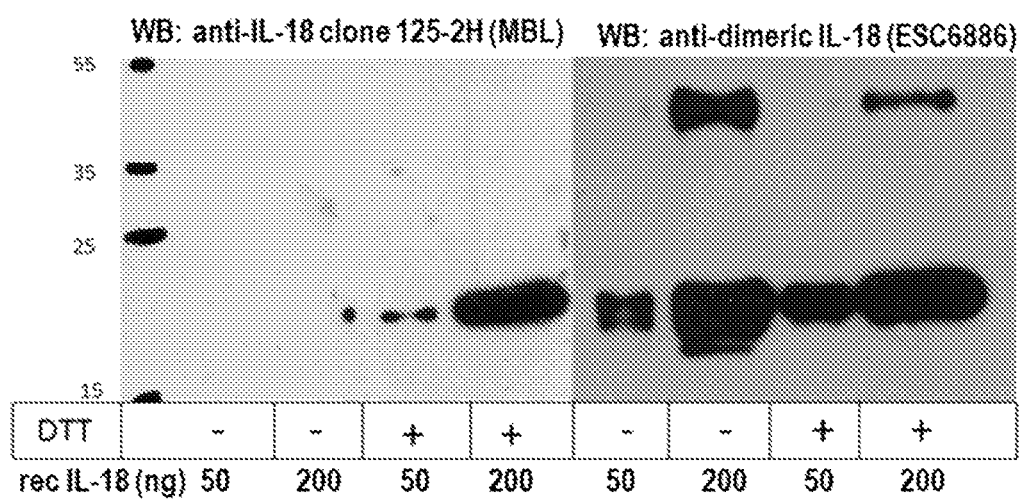
FIG. 3 shows recombinant IL-18 detection using a commercially available anti-IL-18 antibody compared to recombinant IL-18 detection using an anti-IL-18 antibody that binds to dimeric IL-18. Western blot analysis of recombinant IL-18 (50 or 200 ng/lane) in the presence (+) or absence (−) of reducing conditions (DTT) was carried out using a commercially available anti-IL-18 antibody (MBL 125-2H) or HRP-tagged anti-IL-18 antibody ESC6886. No dimeric IL-18 is detected in using the commercially available anti-IL-18 antibody (MBL 125-2H).
Figure 4:
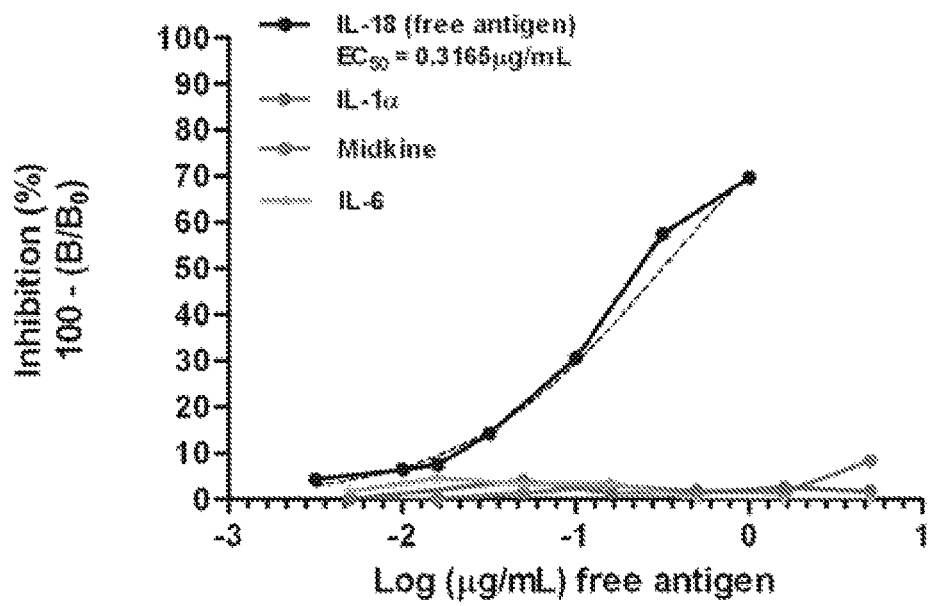
FIG. 4 shows specificity of anti-IL-18 dimer antibodies as tested by competitive cross reactivity assay using HRP-tagged antibody ESC6891 (A) and HRP-tagged antibody ESC6886 (B). IL-18 antigen was bound to the plate at 0.1 µg/ml and signal measured through binding of HRP-tagged anti-IL-18 antibody. The % inhibition is shown through competition for antibody with increasing concentrations of free antigens in solution. Free IL-18 antigen competes with bound IL-18 with an $EC_{50}$ of 0.3165 µg/ml for ESC6891 (A) and 0.175 µg/ml for ESC6886 (B). No crossreactivity was observed for other IL-1 superfamily members such as IL-1a or other cytokines IL-6 or midkine.
Figure 4:
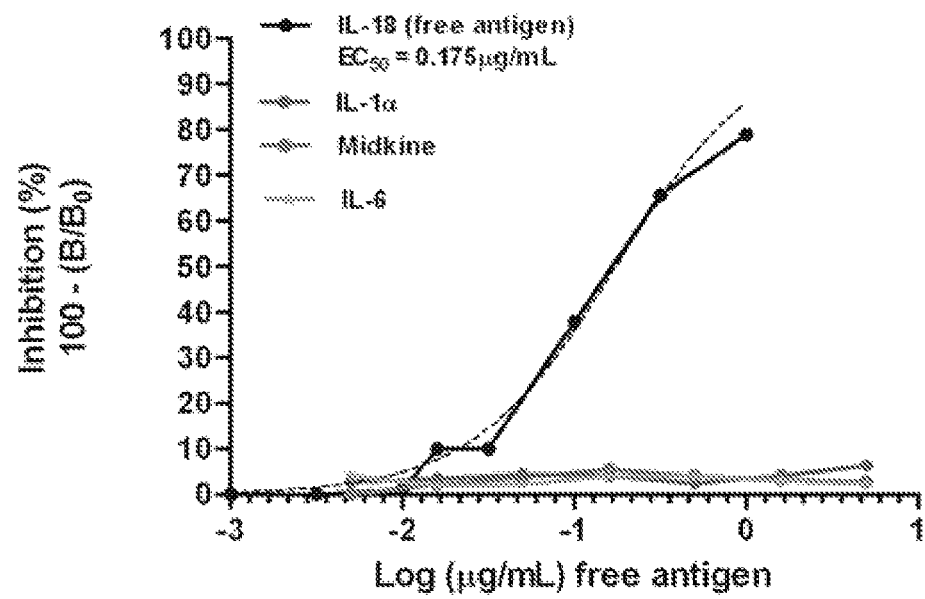

Anti-IL-18 antibody 125-2H obtained from MBL was used to detect recombinant IL-18 by Western blot (FIG. 3). The MBL antibody detected only the monomeric IL-18, while antibody ESC 6886 could detect both monomeric and dimeric IL-18 (FIG. 3). Interestingly, while ESC6886 detected both forms of IL-18 in reducing and in non-reducing conditions, the MBL antibody only detected monomeric IL-18 in reducing conditions (FIG. 3).

Specificity of Anti Dimeric IL-18 Antibodies

Figure 5:
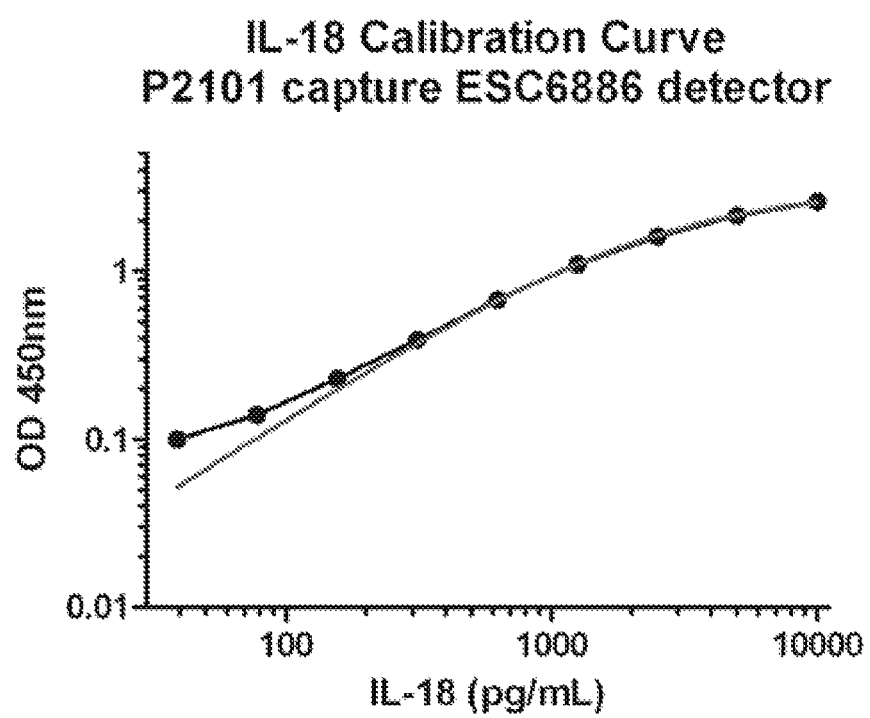
FIG. 5 shows optimisation of an ELISA method for detection of dimeric IL-18. Representative calibration curve for optimisation of an ELISA anti-IL-18 assay using anti-IL-18 antibodies P2100 and P2101 to capture the analyte and using or HRP-tagged anti-IL-18 antibody ESC6886 to detect the analyte without using secondary antibody for visualisation of binding. The calibration curve for the assay range of 39-10000 pg/mL was generated using a non-linear regression function from GraphPad prism software, and the assay had a theoretical limit of sensitivity (mean of blanks+ 2×blank StDev) of 33.8 pg/ml.

Specificity of anti-IL-18 antibody binding to IL-18 antigen was examined using a competitive cross-reactivity assay (FIG. 5). IL-18 antigen was bound to the plate at 0.1 µg/ml, and binding by HRP-tagged antibodies ESC6891 (A) and ESC 6886 (B) to immobilised IL-18 was measured. Cross-reactivity was measured by addition of IL-18, IL-1α, IL-6 and Midkine antigens to reaction wells and measuring competition for binding of the HRP-tagged antibody. The % inhibition is shown through competition for antibody with increasing concentrations of free antigens in solution. Free IL-18 antigen competes with bound IL-18 with an EC50 of 0.3165 µg/ml for ESC6891 (A) and 0.175 µg/ml for ESC6886 (B). No crossreactivity was observed for other IL-1 superfamily members such as IL-1α or other cytokines IL-6 or Midkine.

ELISA Detection of Dimeric IL-18

A sandwich ELISA for detection of total serum IL-18 was optimised for detection with the lowest background. Antibody P2101 was used as capture Ab, and ESC6886 was used as the HRP-conjugated detection Ab (FIG. 5).

This configuration was used to produce a calibration curve which covered an assay range of 39 pg/mL to 10000 pg/mL, with a theoretical limit of sensitivity of 33.8 pg/mL (FIG. 5). These data compared very favourably with other commercial ELISA assays for detection of monomeric IL-18, e.g. ~12 pg/mL-1000 pg/mL (R&D systems), or 78 pg/mL to 5000 pg/mL (e-Bioscience).

Measurement of Dimeric IL-18 to Diagnose Cancer

Figure 6:
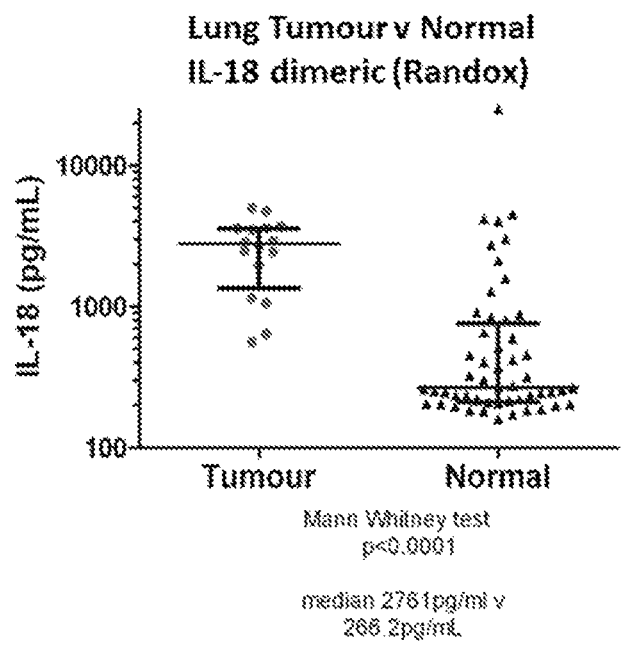
FIG. 6 shows that dimeric IL-18 levels are increased significantly in serum from patients suffering from lung cancer compared to serum from healthy subjects. Median levels of dimeric IL-18 were approximately tenfold higher in serum from lung cancer patients compared to healthy controls (2761 pg/ml vs. 266.2 pg/ml), while median levels of monomeric IL-18 were only marginally different between lung cancer patients and healthy controls (334.1 pg/ml vs. 210.3 pg/ml).
Figure 6:
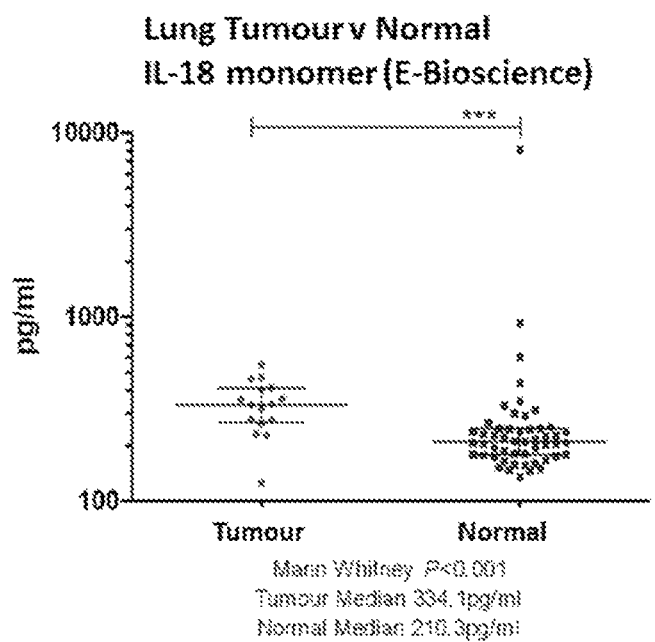

The optimised ELISA assay was used to measure dimeric IL-18 in samples from cancer patient and healthy control subject cohorts, and the same cohort samples were analysed using a commercially available system that measures monomeric IL-18. Results from a lung cancer patient cohort compared to age and gender matched controls are shown in FIG. 6 where dimeric IL-18 is measured using the Randox method while monomeric IL-18 is measured using the E-Bioscience method. The dimeric IL-18 assay showed a highly significant difference between the lung cancer and healthy subject groups, with median values for serum dimeric IL-18 of 2761 pg/mL for cancer patients versus 266.2 pg/mL for healthy controls (p=<0.0001, FIG. 6). The monomeric IL-18 assay showed a very slight difference between the lung cancer and healthy groups (FIG. 6), with a moderate increase in the lung tumour group compared to controls (334.1 pg/mL versus 210.3 pg/mL respectively).

Figure 8:
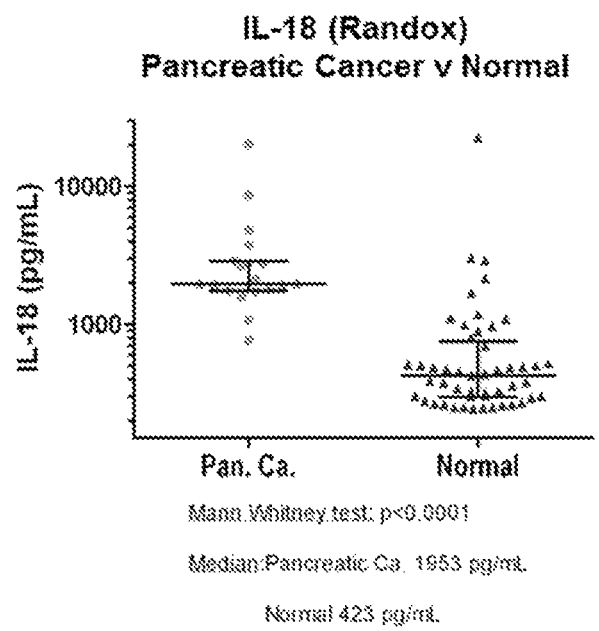
FIG. 8 shows that dimeric IL-18 levels are increased significantly in serum from patients suffering from pancreatic cancer compared to serum from healthy subjects. Median levels of dimeric IL-18 were approximately fivefold higher in serum from pancreatic cancer patients compared to healthy controls (1953 pg/ml vs. 423 pg/ml), while median levels of monomeric IL-18 were only marginally different between pancreatic cancer patients and healthy controls (293.8 pg/ml vs. 158 pg/ml).
Figure 8:
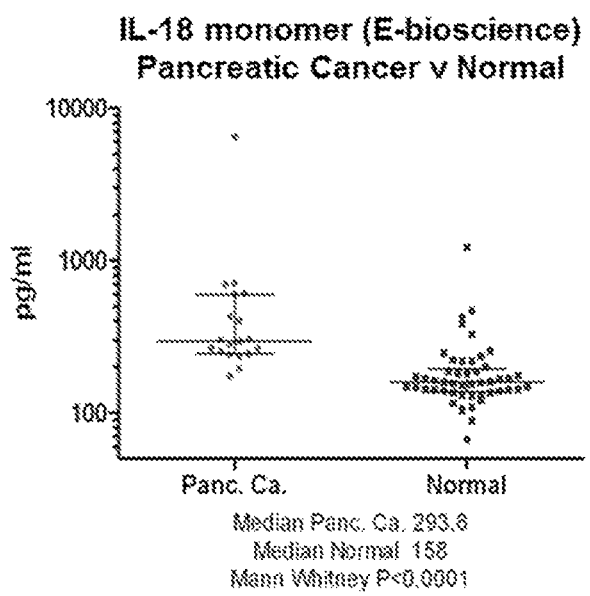

Results from a pancreatic cancer patient cohort compared to age and gender matched controls are shown in FIG. 8 where dimeric IL-18 is measured using the Randox method while monomeric IL-18 is measured using the E-Bioscience method. The dimeric IL-18 assay showed a highly significant difference between the pancreatic cancer and healthy subject groups, with median values for serum dimeric IL-18 of 1953 pg/mL for cancer patients versus 423 pg/mL for healthy controls (p=<0.0001, FIG. 8). The monomeric IL-18 assay showed a very slight difference between the pancreatic cancer and healthy groups (FIG. 8), with a moderate increase in the pancreatic tumour group compared to controls (293.8 pg/mL versus 158 pg/mL respectively).

Figure 10:
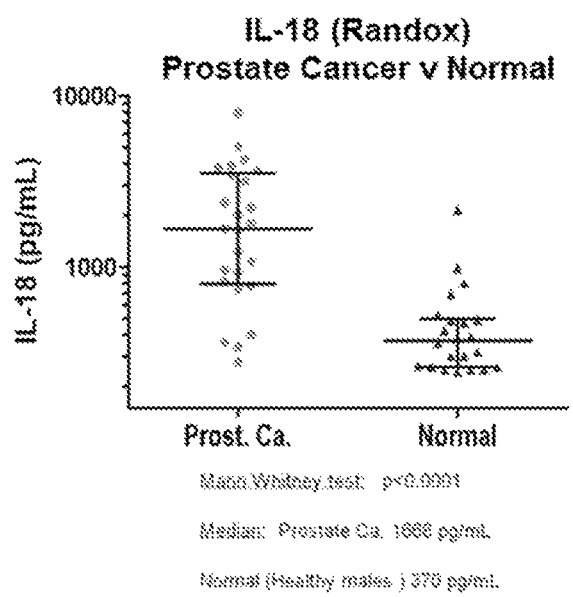
FIG. 10 shows that dimeric IL-18 levels are increased significantly in serum from patients suffering from prostate cancer compared to serum from healthy subjects. Median levels of dimeric IL-18 were approximately fivefold higher in serum from prostate cancer patients compared to healthy controls (1668 pg/ml vs. 370 pg/ml), while median levels of monomeric IL-18 were only marginally different between prostate cancer patients and healthy controls (230.8 pg/ml vs. 164.1 pg/ml).
Figure 10:
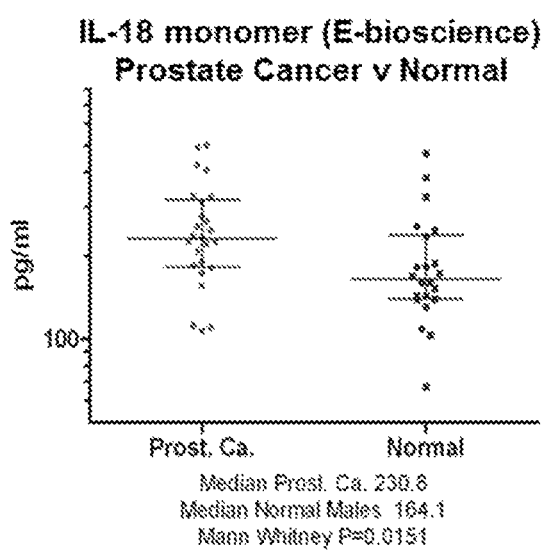

Results from a prostate cancer patient cohort compared to age and gender matched controls are shown in FIG. 10 where dimeric IL-18 is measured using the Randox method while monomeric IL-18 is measured using the E-Bioscience method. The dimeric IL-18 assay showed a highly significant difference between the prostate cancer and healthy subject groups, with median values for serum dimeric IL-18 of 1668 pg/mL for cancer patients versus 370 pg/mL for healthy controls (p=<0.0001, FIG. 10). The monomeric IL-18 assay showed a very slight difference between the prostate cancer and healthy groups (FIG. 10), with a moderate increase in the prostate tumour group compared to controls (230.8 pg/mL versus 164.1 pg/mL respectively).

Measurement of Dimeric IL-18 to Identify Metastases

Figure 12:
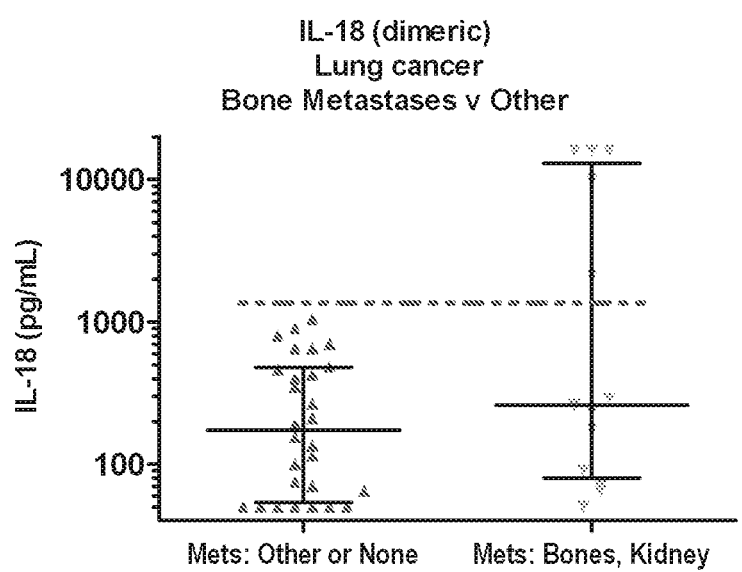
FIG. 12 shows that significantly elevated levels of dimeric IL-18 were associated with bone and kidney metastases in the cohort of subjects suffering from lung cancer—a cut off of >2000 pg/mL offers 100% specificity and 35.7% sensitivity in diagnosing these metastases.
Figure 13:
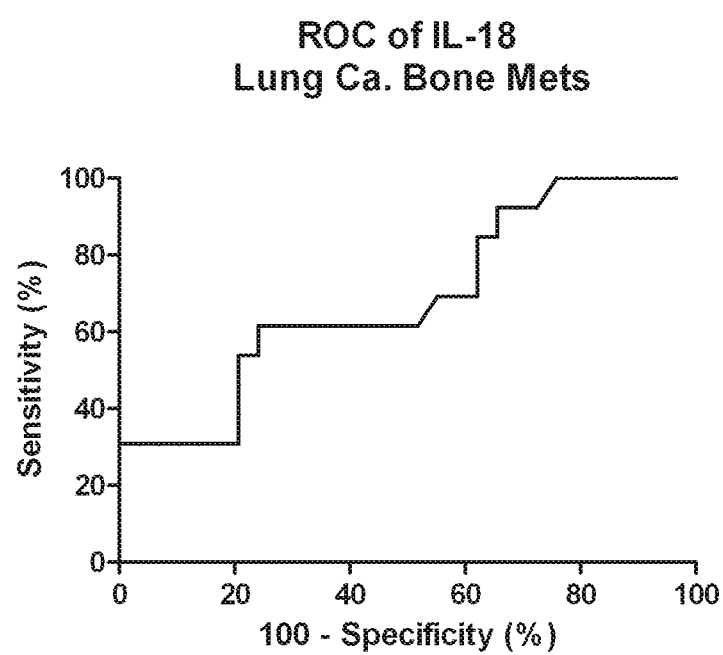
FIG. 13 shows the Receiver Operator Curve for dimeric IL-18 levels in serum from lung cancer patients with bone metastases compared to serum from lung cancer patients without bone metastases, which following binary logistic regression had an AUC=0.69 (p<0.0001).
Figure 14:
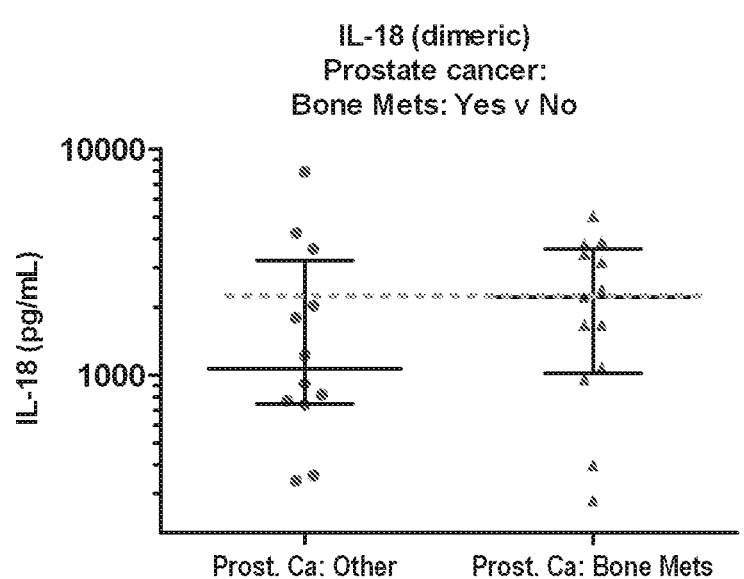
FIG. 14 shows that significantly elevated levels of dimeric IL-18 were associated with bone metastases in the cohort of subjects suffering from prostate cancer—a cut off of >2116 pg/mL offers 75.0% specificity and 53.9% sensitivity in diagnosing these metastases.

We examined levels of dimeric IL-18 in various subgroups of the lung tumour cohort, including those with specific metastases and tumour subtypes. Patients with bone metastases, plus the one patient with a kidney metastasis, showed a moderate increase in median dimeric IL-18 levels (387.9 pg/mL v 249.9 pg/mL, p=NS) compared to those with other metastases or local invasion only. However, all of those lung tumour patients with markedly high levels of dimeric IL-18 had bone or kidney metastasis (FIG. 12). If a cut-off of >2000 pg/mL is set, patients with bone (or kidney) metastasis could be diagnosed with a sensitivity of 35.7% and a specificity of 100%. No differences in dimeric IL-18 levels were found between lung cancer subtypes or other metastases (not shown).

The invention claimed is:

1. A method for measuring and analyzing dimeric interleukin-18 levels in a sample from a subject suffering from a cancer and who is suspected of having metastases comprising:

measuring the amount of dimeric interleukin-18 (IL-18) in a sample obtained from a first subject suffering a cancer, wherein the subject is suspected of having metastases, and determining:
(a) whether the amount of dimeric IL-18 from the first subject's sample is altered in comparison to a sample obtained from a second subject suffering from cancer and not having metastases, and/or
(b) whether the amount of dimeric IL-18 measured from the first subject's sample is above a threshold value for dimeric IL-18.

2. The method according to claim 1, wherein the method determines whether the amount of dimeric IL-18 from the first subject's sample is elevated in comparison to the sample obtained from the second subject.

3. The method according to claim 1, wherein the threshold value is determined from a receiver-operating characteristics graph generated from plotting sensitivity/specificity pairs resulting from continuously varying the decision threshold over an entire range of measured dimeric IL-18 levels.

4. The method according to claim 1, wherein the first subject is suffering from a lung cancer and is suspected or at risk of suffering from bone metastases, and wherein the threshold value for IL-18 is 1050 pg/ml.

5. The method according to claim 1, wherein the metastases are bone or kidney metastases.

6. A method for determining the efficacy of a drug treatment for cancer, comprising:

measuring the amount of dimeric interleukin-18 (IL-18) in a sample obtained from the subject treated with a drug, comparing the measured amount of dimeric IL-18 to that of an untreated sample, and determining whether the drug has had the effect of altering the amount of dimeric IL-18.

* * * * *